(12) United States Patent
Ambrosen et al.

(10) Patent No.: US 9,884,005 B2
(45) Date of Patent: Feb. 6, 2018

(54) AERATED SOLID COSMETIC COMPOSITION

(75) Inventors: Helen Elizabeth Ambrosen, Wimbourne (GB); Margaret Joan Constantine, Poole (GB); Mark Constantine, Poole (GB)

(73) Assignee: COSMETIC WARRIORS LIMITED, Poole, Dorset (GB)

( * ) Notice: Subject to any disclaimer, the term of this patent is extended or adjusted under 35 U.S.C. 154(b) by 721 days.

(21) Appl. No.: 14/129,016

(22) PCT Filed: Jun. 21, 2012

(86) PCT No.: PCT/GB2012/051440
§ 371 (c)(1),
(2), (4) Date: Mar. 27, 2014

(87) PCT Pub. No.: WO2012/175970
PCT Pub. Date: Dec. 27, 2012

(65) Prior Publication Data
US 2014/0220089 A1    Aug. 7, 2014

(30) Foreign Application Priority Data
Jun. 23, 2011 (GB) .................... 1110641.6

(51) Int. Cl.
*A61K 8/92* (2006.01)
*A61K 8/02* (2006.01)
*A61Q 13/00* (2006.01)
*A61Q 19/00* (2006.01)

(52) U.S. Cl.
CPC ............ *A61K 8/922* (2013.01); *A61K 8/0216* (2013.01); *A61Q 13/00* (2013.01); *A61Q 19/00* (2013.01)

(58) Field of Classification Search
None
See application file for complete search history.

(56) References Cited

U.S. PATENT DOCUMENTS

| 4,195,935 | A | * | 4/1980 | Sollich ............... A23G 1/105 366/325.1 |
| 4,889,738 | A | | 12/1989 | Hara |
| 4,919,964 | A | * | 4/1990 | Adams ............... A23D 7/011 426/564 |
| 5,370,888 | A | | 12/1994 | Hachiya et al. |
| 2003/0007943 | A1 | | 1/2003 | Krause et al. |
| 2003/0157050 | A1 | | 8/2003 | Ambrosen et al. |
| 2004/0247531 | A1 | * | 12/2004 | Riedel ............... A61K 8/046 424/47 |
| 2006/0147390 | A1 | | 7/2006 | Schreiber et al. |
| 2006/0270743 | A1 | | 11/2006 | Rossow |
| 2006/0292193 | A1 | | 12/2006 | Lee et al. |
| 2007/0166253 | A1 | | 7/2007 | Kostick et al. |
| 2007/0196298 | A1 | | 8/2007 | Kostick et al. |
| 2008/0089916 | A1 | | 4/2008 | Magee et al. |
| 2008/0193622 | A1 | | 8/2008 | Haedelt et al. |
| 2009/0312213 | A1 | | 12/2009 | Tanaka et al. |
| 2010/0189662 | A1 | | 7/2010 | Neubourg |
| 2012/0107256 | A1 | | 5/2012 | Delvalle et al. |
| 2012/0276030 | A1 | * | 11/2012 | Marthaler ............... A61Q 1/02 424/63 |
| 2016/0193137 | A1 | | 7/2016 | Constantine et al. |

FOREIGN PATENT DOCUMENTS

| CN | 101208013 | 6/2008 |
| DE | 10 2006 051 685 | 5/2006 |
| DE | 10 2006 051 682 | 2/2008 |
| FR | 2 614 313 | 10/1988 |
| GB | 459583 | 1/1937 |
| GB | 2 361 641 | 10/2001 |
| JP | S62-275648 A | 11/1987 |
| JP | H04-234948 A | 8/1992 |
| JP | 2001-199877 A | 7/2001 |
| JP | 2002-145720 A | 5/2002 |
| JP | 2003-531846 A | 10/2003 |
| JP | 2004-256805 A | 9/2004 |
| JP | 2007-501835 A | 2/2007 |
| JP | 2007-169230 A | 7/2007 |
| JP | 2007-197401 A | 8/2007 |
| JP | 2008-024636 A | 2/2008 |
| JP | 2008-247882 A | 10/2008 |
| JP | 2008-539774 A | 11/2008 |
| JP | 2009-040818 A | 2/2009 |
| JP | 2009-508836 A | 3/2009 |
| JP | 2010-506834 A | 3/2010 |
| JP | 2010-168296 A | 8/2010 |
| JP | 2010-530400 A | 9/2010 |
| JP | 4559194 B2 | 10/2010 |
| JP | 2012-531395 A | 12/2012 |
| RU | 2156614 C1 | 9/2000 |

(Continued)

OTHER PUBLICATIONS

Unknown. "Chocolate-based cosmetics pamper sense more than skin." *The HINDU*. (Nov. 15, 2011) http://www.thehindu.com/sci-tech/health/medicine-and-research/chocolatebased-cosmetics-pamper-sense-more-than-skin/article1540660.ece.

International Search report and Written Opinion for International Application No. PCT/GB2012/051440 dated Dec. 18, 2013.

Haedelt et al. "Vacuum-induced Bubble Formation in Liquid-tempered Chocolate." *J. of Food Science*. vol. 70, No. 2. 2005. pp. E159-E162.

Unknown. "Aromatherapy Recipes: How to Make body butter." http://wayback.archive.org/web/20100715072728/http://www.easy-aromatherapy-recipes.com/body-butter-recipe.html. Jul. 15, 2010.

(Continued)

*Primary Examiner* — Abigail Vanhorn
*Assistant Examiner* — Jessica M Kassa
(74) *Attorney, Agent, or Firm* — Merchant & Gould P.C.

(57) ABSTRACT

A solid cosmetic composition includes a vegetable butter. The solid composition has dispersed therein gas bubbles, and the gas bubbles form at least 20% of the volume of the solid cosmetic composition.

22 Claims, No Drawings

(56) References Cited

FOREIGN PATENT DOCUMENTS

| | | |
|---|---|---|
| RU | 2240106 C1 | 11/2004 |
| WO | 00/57715 A1 | 10/2000 |
| WO | WO 01/15543 | 3/2001 |
| WO | WO 2004/056191 | 7/2004 |
| WO | WO 2004/087856 | 10/2004 |
| WO | 2005/006870 A1 | 1/2005 |
| WO | WO 2005/002352 | 1/2005 |
| WO | WO 2006/122823 | 11/2006 |
| WO | 2007/031793 A2 | 3/2007 |
| WO | WO 2009/142275 | 11/2009 |

OTHER PUBLICATIONS

Unknown. "Aromatherapy Recipes: Citrus Mango Body Butter Recipe" http://wayback.archive.org/web/20100715072728/http://www.easyarmatherapy-recipes.com/body-butter-recipe.html. Jul. 17, 2010.

Notice of Decision to Grant for Japanese Patent Application No. 2014-516442, mailed Sep. 1, 2016.

Notice of Decision to Grant for Russian Patent Application No. 2014101928/15, mailed Mar. 18, 2016.

"Lavender Oil", MedlinePlus Medical Encyclopedia, U.S. National Library of Medicine, National Institute of Health, http://www.nlm.nih.gov/medlineplus/ency/article/002711.htm (retrieved Feb. 24, 2015).

* cited by examiner

AERATED SOLID COSMETIC COMPOSITION

This application is a National Stage Application of PCT/GB2012/051440, filed 21 Jun. 2012, which claims benefit of Serial No. 1110641.6, filed 23 Jun. 2011 in Great Britian and which applications are incorporated herein by reference. To the extent appropriate, a claim of priority is made to each of the above disclosed applications.

FIELD OF THE INVENTION

The present invention relates to a solid cosmetic product, a process for producing said product, and a product prepared by the method.

BACKGROUND TO THE INVENTION

The present invention relates to products particularly those for use in contact with the human body.

A cosmetic product which has been increasingly popular is massage bars. These products contain a solidified oil or fat moulded into a product which may be held easily in the hand. Alternatively a larger sized product may be made from which a small piece may be broken and then used. In use, the massage bar is applied to the skin of the recipient either as a complete bar or by breaking off a small piece of product which is then applied to the skin. These solid products are both popular for home use and for application by a professional masseur.

For home use a single solid product which may be applied many times is often considered to be acceptable. However for professional use, for example by a masseur or in a spa, multiple use of a single product is not acceptable. For reasons of hygiene it is not acceptable for one product to be used on one recipient and then later used on a different recipient. This problem may be addressed by use of small pieces of product broken from a larger piece or by providing as small single use size samples. However small pieces often do not provide the same physical sensation to the recipient as being massaged with a larger bar of product. Furthermore if sections are broken from a larger product and used for massage, the broken sections may have rough or sharper edges leading to a less pleasant massage.

The present invention seeks to provide a solid cosmetic product which may be used as a massage bar and which allows for a significantly enlarged bar while avoiding unnecessary waste of the product.

SUMMARY OF THE INVENTION

In a first aspect, there is provided a solid cosmetic composition comprising a vegetable butter wherein the solid composition has dispersed therein gas bubbles, and wherein the gas bubbles form at least 20% of the volume of the solid cosmetic composition.

In a second aspect, there is provided a process for the production of a solid composition solid cosmetic composition comprising a vegetable butter wherein the solid composition has dispersed therein gas bubbles, and wherein the gas bubbles form at least 20% of the volume of the solid cosmetic composition;
the process comprising the steps of:
i) melting one or more vegetable butters;
ii) applying a pressure reduction to the melted butter such that gas bubbles are formed within the melted one or more vegetable butters; and
iii) allowing the mixture of step ii) to solidify.

In a third aspect, there is provided a product obtained or obtainable by a process for the production of a solid composition solid cosmetic composition comprising a vegetable butter wherein the solid composition has dispersed therein gas bubbles, and wherein the gas bubbles form at least 20% of the volume of the solid cosmetic composition;
the process comprising the steps of:
i) melting one or more vegetable butters;
ii) applying a pressure reduction to the melted butter such that gas bubbles are formed within the melted one or more vegetable butters; and
iii) allowing the mixture of step ii) to solidify.

For ease of reference, these and further aspects of the present invention are now discussed under appropriate section headings. However, the teachings under each section are not necessarily limited to each particular section.

Advantages

By forming a cosmetic solid product which has gas bubbles entrapped therein, an aerated solid product is provided. The aerated product has a significantly lower density than the non aerated product. In other words for a given volume a cosmetic product is provided have less mass or in other words containing significantly less cosmetic material. Thus the present invention allows the user to have a hold a product which is of a suitable size and which also offers an enjoyable massage, while containing less cosmetic ingredient thereby minimising waste on disposal or allowing application of all of the product when providing a single massage to individual.

DETAILED DESCRIPTION

Composition

As discussed herein, in one aspect of the present invention, there is provided a solid cosmetic composition comprising a vegetable butter wherein the solid composition has dispersed therein gas bubbles, and wherein the gas bubbles form at least 20% of the volume of the solid cosmetic composition.

It will be understood by one skilled in the art that the nature of a cosmetic product means that the product is not edible. Thus in a further aspect the present invention provides a non-edible solid cosmetic composition comprising a vegetable butter wherein the solid composition has dispersed therein gas bubbles, and wherein the gas bubbles form at least 20% of the volume of the solid cosmetic composition.

The solid products of the present invention are compositions which can substantially sustain their physical shape when unsupported by external means, e.g. packaging etc. Thus, they are considered to be solid, solid like, in solid form or in solid-like form at room temperature. For the avoidance of doubt the solid product must remain substantially solid at up to 30° C.

By solid-like, it is understood that some materials are considered on a day to day basis to be solid, yet over an extremely long period of time, may alter in shape, e.g. amorphous materials such as glass etc. However, they are considered to be solid-like as, for the purpose they fulfil, they are solid.

Due to the solid form of the compositions of the present invention, external packaging is not required to maintain the shape of the composition.

The vegetable butter is a triglyceride which is found to be solid (including solid like, discussed above) at normal usage temperatures. For the avoidance of doubt the vegetable butter is a triglyceride which remains substantially solid at up to 30° C. It will be appreciated however that it is not a requirement that the vegetable butter have a solid fat content of 100% at normal usage temperatures. In a preferred aspect the solid fat has a solid fat content of at least 70%, preferably at least 80%, preferably at least 90%, preferably at least 95%, preferably at least 98%, preferably at least 99% at 25° C.

As discussed herein the gas bubbles which are incorporated into the solid product and entrapped by the solid product form at least 20% of the volume of the solid cosmetic composition. In one preferred aspect the gas bubbles form at least 30% of the volume of the solid cosmetic composition. In one preferred aspect the gas bubbles form at least 40% of the volume of the solid cosmetic composition. In one preferred aspect the gas bubbles form at least 50% of the volume of the solid cosmetic composition. In a further preferred aspect the gas bubbles form at least 60% of the volume of the solid cosmetic composition. In one preferred aspect the gas bubbles form from 20% to 90% of the volume of the solid cosmetic composition. In one preferred aspect the gas bubbles form from 30% to 90% of the volume of the solid cosmetic composition. In one preferred aspect the gas bubbles form from 40% to 90% of the volume of the solid cosmetic composition. In one preferred aspect the gas bubbles form from 50% to 90% of the volume of the solid cosmetic composition. In one preferred aspect the gas bubbles form from 20% to 80% of the volume of the solid cosmetic composition. In one preferred aspect the gas bubbles form from 30% to 80% of the volume of the solid cosmetic composition. In one preferred aspect the gas bubbles form from 40% to 80% of the volume of the solid cosmetic composition. In one preferred aspect the gas bubbles form from 50% to 80% of the volume of the solid cosmetic composition. In one preferred aspect the gas bubbles form from 20% to 70% of the volume of the solid cosmetic composition. In one preferred aspect the gas bubbles form from 30% to 70% of the volume of the solid cosmetic composition. In one preferred aspect the gas bubbles form from 40% to 70% of the volume of the solid cosmetic composition. In one preferred aspect the gas bubbles form from 50% to 70% of the volume of the solid cosmetic composition. In one preferred aspect the gas bubbles form from 60% to 70% of the volume of the solid cosmetic composition.

The gas bubbles may be of any suitable gas. In one aspect the gas bubbles are of a gas selected from air, nitrogen, nitrous oxide, carbon dioxide and mixtures thereof.

The present invention provides a cosmetic product which is solid. The vegetable butters incorporated into the solid product are typically used as agents in massage. However the solid cosmetic product of the present invention may be used in any manner in which the end user sees fit. However, in a preferred aspect the solid cosmetic composition of the present invention is a massage bar.

The composition of the present invention is typically made by moulding of an aerated product. Thus in one aspect the product of the present invention is prepared by melting and then aerating the ingredients of the product, placing the melted aerated product into a mould and allowing the aerated product to set. The aerated product is then released from the mould once solid. This process is described in further detail herein. It has been found that when an aerated product is formed in a mould it may be difficult to remove the aerated product from the mould because of the multiple points of contact between the aerated structure and the mould itself. To alleviate these problems of mould release it is desirable to coat the inside of the mould with a small amount of shell material and then form within this the solidified aerated product. Thus in a further preferred aspect the composition of the present invention comprises a shell coating. This shell coating is typically made from the same composition as the aerated product but which has not been aerated itself. Thus in a preferred aspect the shell coating is formed from the same material as the solid composition having dispersed therein gas bubbles from the same composition as the aerated product. In one aspect the shell is made from a different composition to the aerated product. In one aspect the shell is made from at least the same ingredients as the aerated part of the product but in different amounts or in the absence of optional ingredients present in the aerated part of the product. Thus in a further aspect there is provided a solid cosmetic product comprising (a) a core material comprising a vegetable butter wherein the core material has dispersed therein gas bubbles, (b) a shell material comprising a vegetable butter, wherein the shell material at least partially encases the core material wherein the gas bubbles form at least 20% of the volume of the solid cosmetic composition.

Vegetable Butter

The solid cosmetic product of the present invention must contain at least one vegetable butter. The term vegetable butter is understood by one skilled in the art and means a triglyceride obtainable from vegetable source which has the consistency of a butter. Vegetable butters include Aloe butter, Avocado butter, Cocoa butter, Coffee Bean butter, Cupuacu butter, Refined butter, Hemp Seed butter, Illipe butter, Kokum butter, Macadamia Nut butter, Mango butter, Mochacchino butter, Murumuru butter, Olive butter, Pistachio Nut butter, Shea butter, coconut butter, Shealoe butter and Sweet Almond butter. In a preferred aspect the vegetable butter is selected from murumuru butter, illipe butter, mango butter, avocado butter, cupuacu butter, coconut butter, cocoa butter, shea butter and mixtures thereof. In a preferred aspect the vegetable butter is selected from cocoa butter, shea butter and mixtures thereof.

Preferably the vegetable butter is a mixture of two or more vegetable butters. In a highly preferred aspect the vegetable butter is a mixture of cocoa butter and shea butter.

When cocoa butter is used in the present invention, the cocoa butter may optionally be combined with cocoa solids. When the cocoa butter is combined with cocoa solids it may give the appearance of a chocolate type product.

The vegetable butter may be present in any amount to provide the desired physical characteristics of the solid cosmetic product. Preferably the vegetable butter is present in an amount of from about 10% to about 99% by weight of the total composition. Preferably the vegetable butter is present in an amount of from about 20% to about 99% by weight of the total composition. Preferably the vegetable butter is present in an amount of from about 30% to about 99% by weight of the total composition. Preferably the vegetable butter is present in an amount of from about 40% to about 99% by weight of the total composition. Preferably the vegetable butter is present in an amount of from about 50% to about 99% by weight of the total composition. Preferably the vegetable butter is present in an amount of from about 60% to about 99% by weight of the total composition. Preferably the vegetable butter is present in an amount of from about 70% to about 99% by weight of the total composition. Preferably the vegetable butter is present in an amount of from about 80% to about 99% by weight of the total composition. Preferably the vegetable butter is present in an amount of from about 85% to about 99% by weight of the total composition. Preferably the vegetable butter is present in an amount of from about 90% to about 99% by weight of the total composition. Preferably the vegetable butter is present in an amount of from about 95% to about 99% by weight of the total composition. Preferably the vegetable butter is present in an amount of approximately 97% by weight of the total composition.

When the solid cosmetic product contains cocoa butter, the cocoa butter may be present in any suitable amount. Typically the cocoa butter is present in an amount of from about 5% to about 94% by weight of the total composition. Preferably the cocoa butter is present in an amount of from about 10% to about 94% by weight of the total composition. Preferably the cocoa butter is present in an amount of from about 20% to about 94% by weight of the total composition. Preferably the cocoa butter is present in an amount of from about 30% to about 94% by weight of the total composition. Preferably the cocoa butter is present in an amount of from about 40% to about 94% by weight of the total composition. Preferably the cocoa butter is present in an amount of from about 50% to about 94% by weight of the total composition. Preferably the cocoa butter is present in an amount of from about 60% to about 94% by weight of the total composition. Preferably the cocoa butter is present in an amount of from about 70% to about 94% by weight of the total composition. Preferably the cocoa butter is present in an amount of from about 70% to about 90% by weight of the total composition. Preferably the cocoa butter is present in an amount of from about 75% to about 85% by weight of the total composition. Preferably the cocoa butter is present in an amount of approximately 80% by weight of the total composition.

When the solid cosmetic product contains shea butter, the shea butter may be present in any suitable amount. Typically the shea butter is present in an amount of from about 5% to about 94% by weight of the total composition. Preferably the shea butter is present in an amount of from about 5% to about 90% by weight of the total composition. Preferably the shea butter is present in an amount of from about 5% to about 80% by weight of the total composition. Preferably the shea butter is present in an amount of from about 5% to about 70% by weight of the total composition. Preferably the shea butter is present in an amount of from about 5% to about 60% by weight of the total composition. Preferably the shea butter is present in an amount of from about 5% to about 50% by weight of the total composition. Preferably the shea butter is present in an amount of from about 5% to about 40% by weight of the total composition. Preferably the shea butter is present in an amount of from about 5% to about 30% by weight of the total composition. Preferably the shea butter is present in an amount of from about 5% to about 25% by weight of the total composition. Preferably the shea butter is present in an amount of from about 10% to about 25% by weight of the total composition. Preferably the shea butter is present in an amount of from about 10% to about 20% by weight of the total composition. Preferably the shea butter is present in an amount of from about 15% to about 25% by weight of the total composition. Preferably the shea butter is present in an amount of from about 15% to about 20% by weight of the total composition. Preferably the shea butter is present in an amount of approximately 17% by weight of the total composition.

Additional Components

The solid product of the present invention may also comprise one or more cosmetically acceptable additives. The person skilled in the art is aware of a range of cosmetically acceptable additives which are suitable for incorporation into such compositions. For example, binders, fillers, opacifiers, perfumes, fragrances, decorative items and mixtures thereof.

It is particularly preferred that the composition of the present invention further comprises a fragrance. Preferably the fragrance is selected from essential oils. Preferably the fragrance, and more preferably the essential oil, is present in an amount of from about 0.5% to about 4% by weight of the total composition. More preferred amounts are from about 0.5% to about 3.5% by weight of the total composition, such as from about 0.5% to about 3% by weight of the total composition, such as from about 1% to about 3% by weight of the total composition, such as from about 1.5% to about 2.5% by weight of the total composition, such as approximately 2% by weight of the total composition.

Fruit and herb extracts and juices, vegetable oils and essential oils are all compatible with the composition. Colours, both naturally derived and synthetic can be used to colour the product.

In one embodiment, the cosmetically acceptable additives are selected from the group consisting of essential oils, vitamins, fragrances, colourings, clays, decorative articles and mixtures thereof.

The essential oils may be selected based on the fragrance desired, skin type to be treated and other effects desired based on the well known properties of essential oils. The addition of essential oils, when taken in to the nose, are known to alter mood. For example, essential oils are known to create effects of drowsiness or stimulating the senses. Many well documented effects can be achieved by the use of essential oils.

In one embodiment, the one or more essential oils present in the solid product are selected from Tarragon, Lemon myrtle, Jasmin, Ylang ylang, Labdunum, Lemongrass, Rose otto, Grapefruit, Patchouli, Rosemary, Armois, Lemon, Neroli, Sweet violet, Lavender, Orange 50 fold, Vanilla, Peppermint, Benzoin, Hydrangia, Litsea Cubeba, Cardamon, Tonka, and Chamomile blue. In one embodiment, the one or more essential oils present in the solid product are selected from Tarragon, Lemon myrtle, Labdunum, and Lemon.

Vitamins, particularly B, C and E are very beneficial for the skin. Vitamin rich ingredients such as Wheatgerm oil can also be used to deliver vitamins on to the skin. In a one embodiment, the vitamins are selected from vitamin B, vitamin C, vitamin E and mixtures thereof. It will be appreciated by one skilled in the art that the vitamin may be provided from any suitable source. For example the vitamin(s) may be provided from a synthetic source or from incorporation into the solid product of a material, such as a natural material, that has a high vitamin content.

The ingredients in the present invention do not require cosmetic preservatives. The use of cosmetic preservatives can increase the potential to irritate the skin.

The decorative items which may be present in the solid product include items such as glitter, paper such as rice paper, sequins, dried or fresh flowers, herbs, vegetables, parts thereof or mixtures thereof. Other enhancing materials may also be incorporated Further preferred additive materials include vegetable oils, chocolate, herbs and spices, cosmetic colours (e.g. paprika, gardenia extract, dmc red no. 30), beans (e.g. aduki), fruit, fresh or dried (e.g. banana), honey, glycerin, cosmetic glitter, other vegetable butters (e.g. mango, avocado), clays (e.g. kaolin), starches (e.g. corn starch) and mixtures thereof.

The above ranges provide preferred amounts of each of the components. Each of these ranges may be taken alone or combined with one or more other component ranges to provide a preferred aspect of the invention.

One highly preferred composition accordance with the present invention comprises
(i) cocoa butter in an amount of from about 70% to about 90% by weight of the total composition
(ii) shea butter in an amount of from about 10% to about 25% by weight of the total composition
(iii) fragrance in an amount of from about 2% to about 4% by weight of the total composition.

Process

As discussed herein, the invention provides a process for the production of a solid cosmetic composition comprising a vegetable butter wherein the solid composition has dispersed therein gas bubbles, and wherein the gas bubbles form at least 20% of the volume of the solid cosmetic composition;
the process comprising the steps of:
i) melting one or more vegetable butters;
ii) applying a pressure reduction to the melted butter such that gas bubbles are formed within the melted one or more vegetable butters; and
iii) allowing the mixture of step ii) to solidify.

The shape of the solid products of the present invention is not limited. It may be that the solid products are provided with a shape which would be aesthetically pleasing and/or which aids in the use of the product. For example, it may be that the solid product is produced in such a manner so that it solidifies in a shape which is ergonomically acceptable to the user. Therefore, in one embodiment of the process of the present invention, the mixture of step i) and/or step ii) is pressed into a mould, allowed to solidify, and then turned out to produce the solid product.

As described herein, the solid product may further comprise one or more cosmetically acceptable additives. In one embodiment, the process further comprises the step of combining with the mixture of step i) and/or step ii) one or more cosmetically acceptable additives as defined herein and/or the dispersant defined herein.

The process of the present invention requires that a pressure reduction be applied to the melted butter such that gas bubbles are formed within the melted one or more vegetable butters. This pressure reduction may be applied from any starting pressure. For example in one aspect the melted vegetable butter may be held under increased pressure, that is a pressure of greater than 1 atmosphere. This may be achieved by applying increased air pressure or increased pressure of another gas such as nitrogen, nitrous oxide or carbon dioxide. The pressure may then be reduced either to a lower pressure which is still greater than 1 atmosphere, to a pressure of 1 atmosphere or to a pressure of less than 1 atmosphere. In a further possibility the melted vegetable butter may be initially held at 1 atmosphere and then a vacuum applied. By vacuum it is meant a complete or partial vacuum i.e. a pressure of less than 1 atmosphere.

The present invention also provides a product obtained or obtainable by a process for the production of a solid composition solid cosmetic composition comprising a vegetable butter wherein the solid composition has dispersed therein gas bubbles, and wherein the gas bubbles form at least 20% of the volume of the solid cosmetic composition;
the process comprising the steps of:
i) melting one or more vegetable butters;
ii) applying a pressure reduction to the melted butter such that gas bubbles are formed within the melted one or more vegetable butters; and
iii) allowing the mixture of step ii) to solidify.

Method

In one aspect of the present invention, there is provided a method comprising contacting the skin of a user with water in which the solid product as defined herein has dissolved or in which the solid product as defined herein is dissolving. In a typical method water in run in to the bath at acceptable temperature. The user immerses their body in the water and the solid product is dropped in to the water. The user then watches the effect of the product on the surface of the water or as it effervesces beneath the surface. The user then bathes in the water.

EXAMPLES

The invention will now be described with reference to the following non-limiting example.

A solid product having the following composition was prepared.

The formula was as follows:

| Ingredient | Grams | % by weight |
|---|---|---|
| Cocoa Butter | 80 | 80 |
| Shea Butter | 17 | 17 |
| Fragrance (Lavender oil) | 3 | 3 |

Method

The Cocoa Butter and Shea Butter were warmed gently to melt. The fragrance was added and the mixture cooled to below 30° C.

The mixture was poured into a canister suitable for the preparation of whipped cream. A cylinder of nitrous oxide was attached and the nitrous oxide discharged into the mixture and shaken. The canister contents were dispensed into a mould. The mould was chilled and left to set completely.

After the product has set it was released from the mould and the weight of the product determined. This was repeated in quadruplicate.

For comparison, the above formula was filled into the same mould without being subjected to pressure reduction. Thus the comparison product was not aerated. After the product has set it was released from the mould and the weight of the comparison product also determined. This was repeated in duplicate.

| | Non Aerated | | Aerated | | | |
|---|---|---|---|---|---|---|
| Sample No | 1 | 2 | 3 | 4 | 5 | 6 |
| Weight (g) | 73.64 | 73.95 | 33.67 | 20.55 | 24.14 | 19.94 |
| Average Weight (g) | 73.795 | | | 24.575 | | |
| % Gas | | | 54% | 72% | 67% | 73% |

From the average of the weights, it was possible to calculate that approximately 33% (24.575 g/73.795 g) of the aerated product volume was provided by the formulation. The remaining 67% was provided by the dispersed gas.

Alternative production processes are:

Method 2

Warm the Cocoa Butter and Shea Butter gently to melt. Add the fragrance and cool to below 30° C. Pour the mixture into a suitable vessel. Using a mechanical emulsifier, aerate the mixture. Dispense into moulds, chill and leave to set completely.

Method 3.

Warm the Cocoa Butter and Shea Butter gently to melt. Add the fragrance and cool to below 30° C. Put the mixture in to a suitable vessel. Withdraw the air from the mixture by creating a vacuum to aerate. Pour into moulds and leave to set.

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

The invention claimed is:

1. A solid non-edible cosmetic composition comprising:
   (a) a core material comprising a vegetable butter wherein the core material has dispersed therein gas bubbles,
   (b) a shell material comprising a vegetable butter, wherein the shell material at least partially encases the core material,
   wherein the composition comprises from 60 to 99% of a vegetable butter by weight of the total composition,
   wherein the gas bubbles form from 20 to 70% of the volume of the solid cosmetic composition, wherein solid means that the non-edible cosmetic composition can sustain its physical shape when externally unsupported, and
   wherein the solid non-edible cosmetic composition is solid at room temperature and remains solid at up to a temperature of 30° C.

2. The solid non-edible cosmetic composition according to claim 1, wherein the vegetable butter is a mixture of two or more vegetable butters.

3. The solid non-edible cosmetic composition according to claim 1, wherein the vegetable butter is selected from aloe butter, avocado butter, cocoa butter, coffee bean butter, cupuacu butter, refined butter, hemp seed butter, illipe butter, kokum butter, macadamia nut butter, mango butter, mochacchino butter, murumuru butter, olive butter, pistachio nut butter, shea butter, coconut butter, shealoe butter, sweet almond butter and mixtures thereof.

4. The solid non-edible cosmetic composition according to claim 3, wherein the vegetable butter is a mixture of cocoa butter and shea butter.

5. The solid non-edible cosmetic composition according to claim 1, wherein the vegetable butter is present in an amount of from about 80% to about 99% by weight of the total composition.

6. The solid non-edible cosmetic composition according to claim 1, comprising cocoa butter in an amount of from about 5% to about 94% by weight of the total composition.

7. The solid non-edible cosmetic composition according to claim 6, comprising cocoa butter in an amount of from about 70% to about 90% by weight of the total composition.

8. The solid non-edible cosmetic composition according to claim 1, comprising shea butter in an amount of from about 5% to about 94% by weight of the total composition.

9. The solid non-edible cosmetic composition according to claim 8, comprising shea butter in an amount of from about 10% to about 20% by weight of the total composition.

10. The solid non-edible cosmetic composition according to claim 1, further comprising a fragrance.

11. The solid non-edible cosmetic composition according to claim 10, wherein the fragrance comprises essential oils.

12. The solid non-edible cosmetic composition according to claim 10, comprising the fragrance in an amount of from about 0.5% to about 4% by weight of the total composition.

13. The solid non-edible cosmetic composition according to claim 1, comprising:
   (i) cocoa butter in an amount of from about 70% to about 85% by weight of the total composition;
   (ii) shea butter in an amount of from about 10% to about 25% by weight of the total composition; and
   (iii) fragrance in an amount of from about 2% to about 4% by weight of the total composition.

14. The solid non-edible cosmetic composition according to claim 1, further comprising at least one additional component selected from binders, fillers, opacifiers, perfumes, fragrances, decorative items and mixtures thereof.

15. The solid non-edible cosmetic composition according to claim 1, wherein the gas bubbles form from 40% to 70% of the volume of the solid cosmetic composition.

16. The solid non-edible cosmetic composition according to claim 1 wherein the composition is a massage bar.

17. The solid non-edible cosmetic composition according to claim 1 wherein the shell material is formed from the same material as the core material having dispersed therein gas bubbles.

18. A process for the production of a solid composition as defined in claim 1 comprising the steps of:
   i) melting one or more vegetable butters;
   ii) applying a pressure reduction to the melted butter such that gas bubbles are formed within the melted one or more vegetable butters;
   iii) coating the inside of a mould with an amount of shell material and
   iii) allowing the mixture of step ii) to solidify within the coated mould to form a solidified aerated core material at least partially encased in the shell material.

19. A process according to claim 18, wherein the mixture of step ii) is caused to solidify in a predetermined shape.

20. A process according to claim 18 wherein the pressure reduction is provided by applying a pressure of greater than 1 atmosphere to the melted product and then subsequently reducing the pressure.

21. A process according to claim 18 wherein the pressure reduction is provided by applying a pressure of less than 1 atmosphere to the melted product.

22. A cosmetic method comprising contacting the skin of a user with a solid cosmetic composition as defined in claim 1.

* * * * *